United States Patent [19]

Zeger et al.

[11] 4,428,237
[45] Jan. 31, 1984

[54] SYSTEM AND METHOD FOR MEASURING ULTRASONIC RETURN SIGNALS

[75] Inventors: Andrew E. Zeger; Burton S. Abrams, both of Wyndmoor; Joseph L. Rose, Churchville; Michael J. Avioli, Jr., Havertown, all of Pa.; Gurvinder P. Singh, San Antonio, Tex.

[73] Assignee: Electric Power Research Institute, Inc., Palo Alto, Calif.

[21] Appl. No.: 206,626

[22] Filed: Nov. 13, 1980

[51] Int. Cl.³ .............................................. G01N 29/04
[52] U.S. Cl. .......................................... 73/592; 73/602
[58] Field of Search ................. 73/592, 602, 614, 627, 73/1 DV; 364/507, 582

[56] References Cited

U.S. PATENT DOCUMENTS

| 3,453,871 | 7/1969 | Krautkramer | 73/602 |
| 3,756,071 | 9/1973 | Dory | 73/602 |
| 4,290,308 | 9/1981 | Dau | 73/602 |

Primary Examiner—Anthony V. Ciarlante
Attorney, Agent, or Firm—Flehr, Hohbach, Test, Albritton & Herbert

[57] ABSTRACT

An ultrasonic return signal analyzing instrument and method including analog circuitry for making partial power measurements on two selected frequency bands of the frequency spectrum of an ultrasonic return signal waveform and digital circuitry for measuring selected features of the envelope of the ultrasonic return signal waveform. Digital waveform measurements are converted to analog signals and then combined in an algorithmic combining circuit to produce a test statistic signal. A decision circuit receives the test statistic signal and registers a decision on a characteristic of the structure under examination based on the value of the test statistic signal. The instrument includes a signal normalization circuit to normalize the ultrasonic return signal to a fixed peak value and includes a frequency up-converter in the normalizing circuit and frequency down-converters in the partial power measurement circuits for increasing the accuracy of peak detection in the normalizing circuit and envelope detection for the partial power band signals and the total power signal. The digital waveform feature measurement circuitry includes circuitry for measuring the rise time and duration time of the ultrasonic return signal envelope and logic is provided for handling two distinct return signal waveforms with rise time and duration time measurements being accomplished on the highest distinct pulse within the GATE signal window of the instrument. A GATE signal generated from the delayed GATE input of the pulser receiver of an ultrasonic instrument is utilized to GATE the various measurement functions so that measurements will be made only on the selected segment of the ultrasonic return signal waveform desired to be analyzed. A Fisher linear discriminant function is used as the algorithm in connection with analyzing ultrasonic return signals from stainless steel pipe having possible intergranular stress corrosion cracking conditions therein.

16 Claims, 12 Drawing Figures

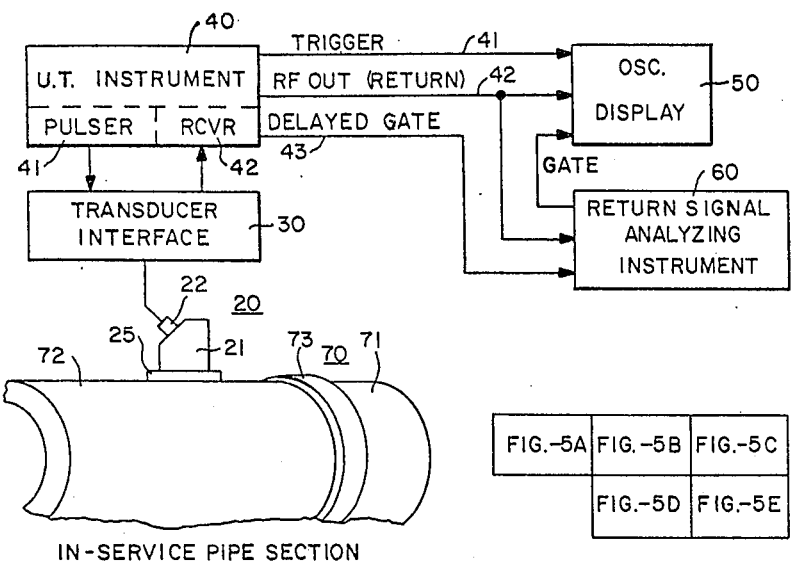
FIG.—1
FIG.—5F
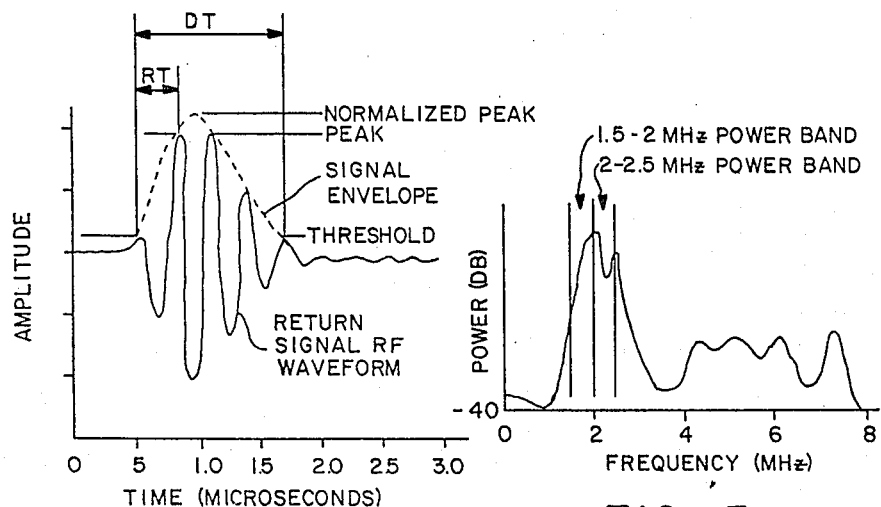
FIG.—2
FIG.—3

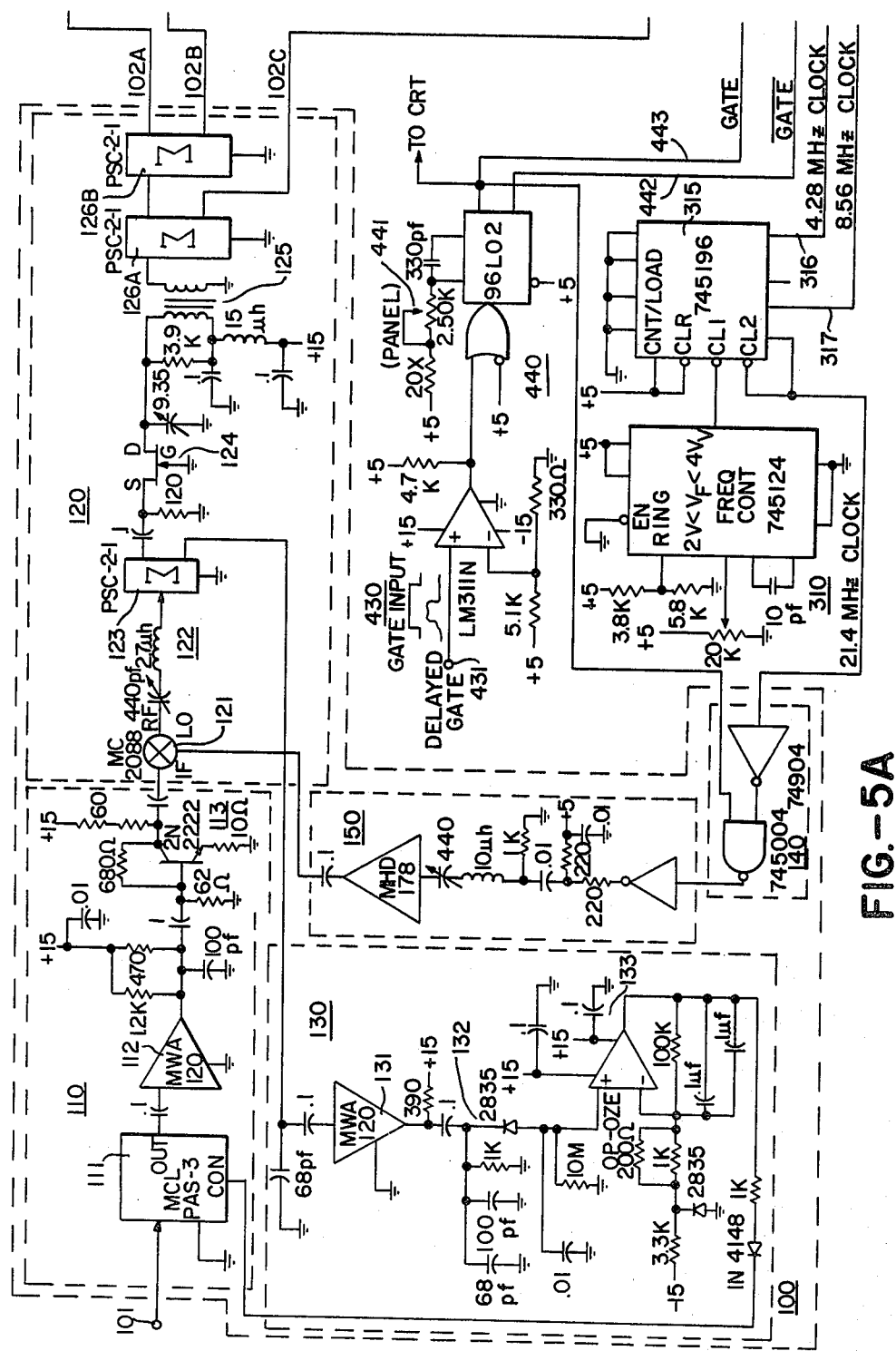
FIG.—5A

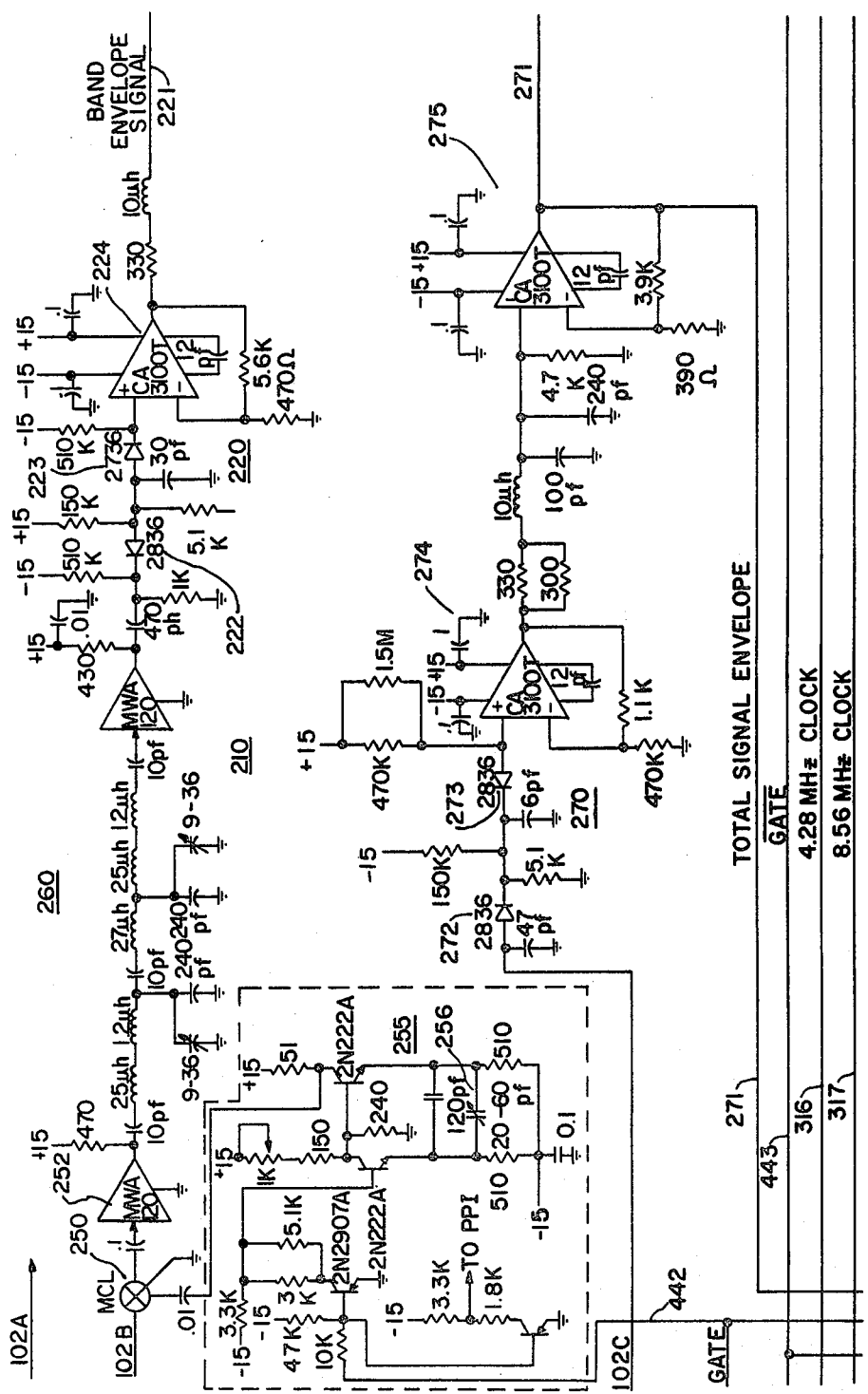
FIG.—5B

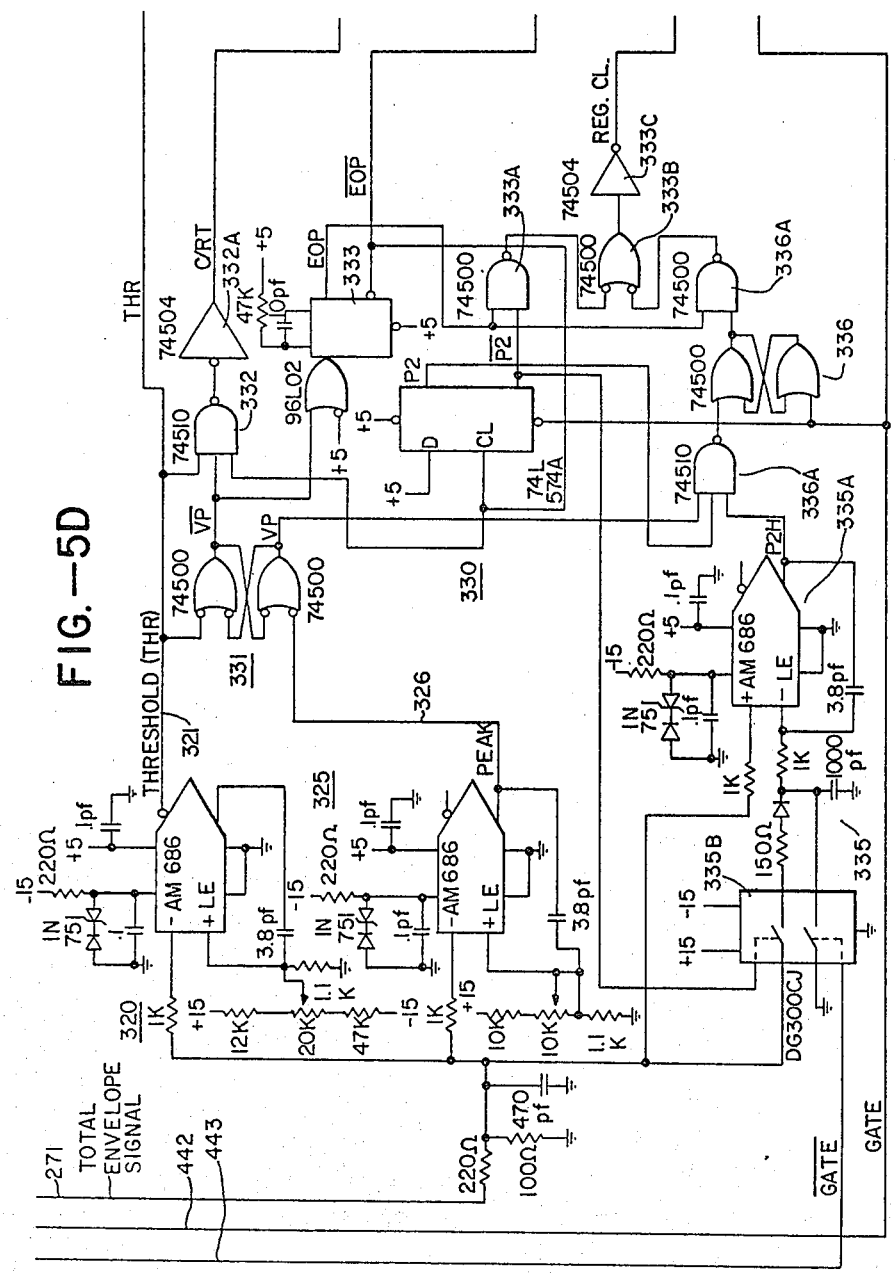
FIG.—5D

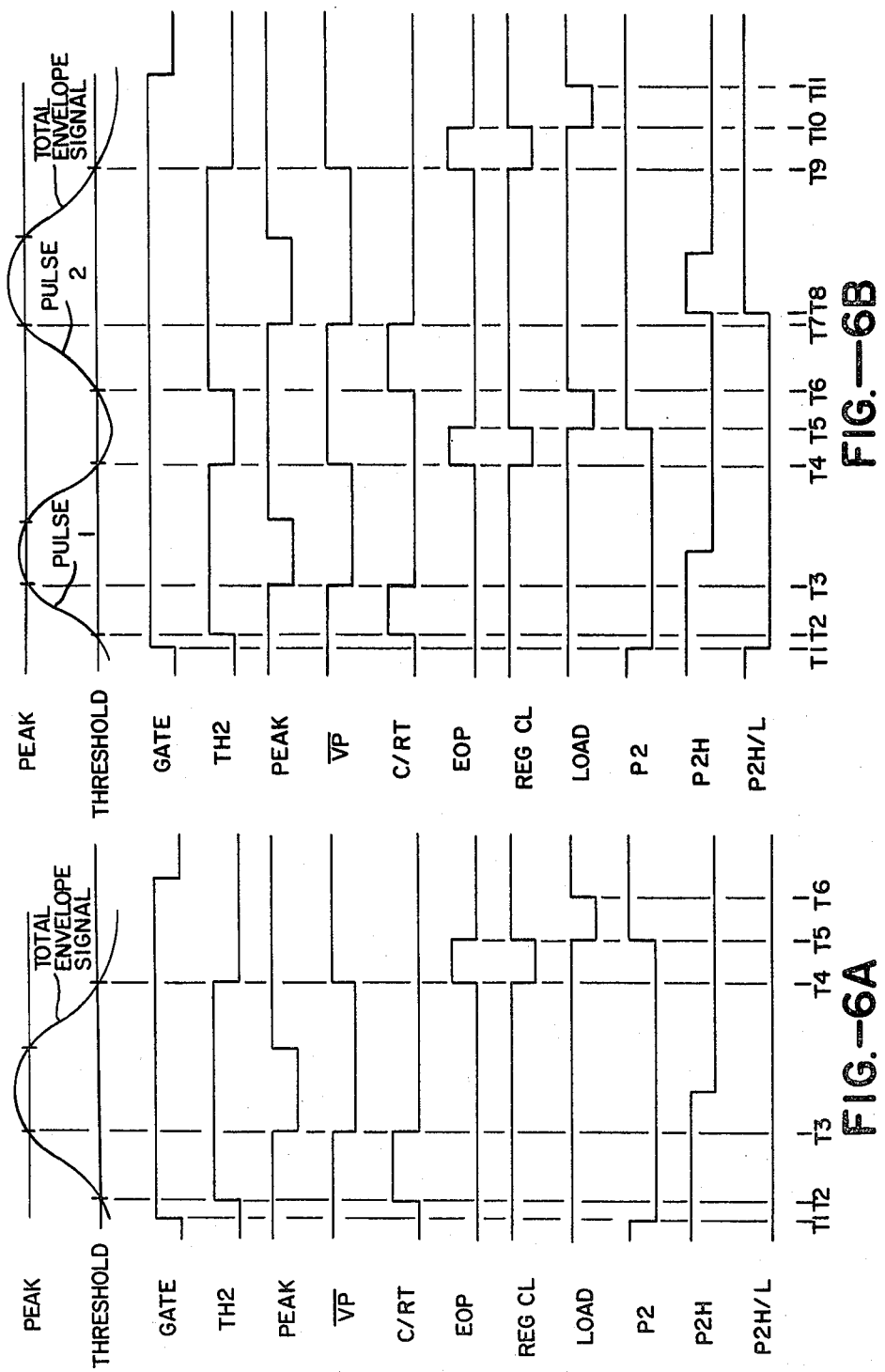

SYSTEM AND METHOD FOR MEASURING ULTRASONIC RETURN SIGNALS

This invention relates generally to ultrasonic testing apparatus and methods and specifically to systems and methods for analyzing ultrasonic return signals which characterize a structure being examined. More specifically, this invention relates to a system and method for analyzing certain features of the frequency spectrum and waveform of an ultrasonic return signal from a structure being examined.

Manual ultrasonic testing is a type of nondestructive examination often used to ascertain the integrity of in-service structural components such as, for example, piping systems in power plants. Manual ultrasonic testing apparatus conventionally includes a transducer assembly, a transducer interface circuit, an ultrasonic test instrument, and an oscilloscope display. The transducer assembly generally includes an ultrasonic transducer and a coupling block for coupling signal energy between the object under investigation and the transducer with a viscous liquid couplant generally employed between the coupling block and the actual object itself. The ultrasonic test instrument conventionally includes a pulser and a receiver. A typical methodology of conventional manual ultrasonic testing involves an initial calibration of the ultrasonic test instrumentation utilizing a calibration block with a sample flaw. The calibration block is utilized in conjunction with placement of the transducer assembly at various positions to construct a distance amplitude correction (DAC) curve which generally permits correlation of the peak amplitude of the ultrasonic return signal with the distance of the sample flaw from the transducer. The DAC curve is generally marked on the oscilloscope screen so that in subsequent use of the equipment to examine an unknown structure, the return signals from the unknown structure can be compared on a distance-amplitude basis with the DAC curve as a basis for judging the existence of a possible structural flaw at a particular location on the component being tested.

In testing situations where flaw sizes are large and return signals from suspected flaws are readily distinguished from return signals from geometric reflectors in the structure being tested, conventional manual ultrasonic testing is a generally satisfactory approach to ascertaining the structural integrity of the particular component. In some testing situations, however, the return signals from actual flaws are difficult to distinguish from return signals from geometric reflectors on the basis of comparison of the return signal with a reference DAC curve. One such testing situation is the examination of stainless steel pipe systems in boiling water nuclear power plants for intergranular stress corrosion cracking conditions. One of the main components of every boiling water nuclear power plant is a stainless steel piping system which typically involves sections of stainless steel piping welded together to carry a liquid such as reactor coolant which is, of course, a critical portion of the nuclear power plant.

Intergranular stress corrosion cracking (IGSCC) is a major degradation mechanism in stainless steel piping systems of boiling water nuclear power plants. IGSCC conditions in stainless steel piping systems most often occur in regions adjacent to weld areas in the pipe sections and are generally thought to originate on the interior walls of the pipe near the weldment and then grow both radially and circumferentially into the pipe section due to the combined effect of stress, heat, and corrosion from the oxygenated liquid passing through the pipe. Typically, IGSCC conditions in a pipe are called "tight" cracks which visually appear as fissures or veins extending throughout a volume of the pipe.

Several of the qualities of IGSCC conditions and the stainless steel pipe medium in which they occur render the detection of the IGSCC condition difficult with conventional UT methods. The tightness of the intergranular stress corrosion cracks results in an ultrasonic return signal from the discontinuity which is generally small in amplitude. Furthermore, the material of typical stainless steel piping has grains which represent acoustic discontinuities which sometimes produce UT return signals of an amplitude generally comparable to return signals from IGSCC conditions. In addition, the IGSCC conditions often occur in regions of the pipe section which include a substantial number of other geometric reflectors which may produce return signals of comparable or larger magnitude to those of the IGSCC condition. Consequently, detection of IGSCC conditions in stainless steel piping systems of nuclear power plants is a difficult process utilizing manual conventional UT apparatus and methods.

Nuclear power plant inspection requirements generally mandate a conservative replacement approach because of the risks involved in leakages from power plant piping systems. Large stainless piping is often used in the primary reactor coolant system. If conventional UT inspection based on current standards produces an indication of a possible critical IGSCC condition, conservative replacement criteria may mandate unplanned shutdown of the reactor. Such a reactor outage may cost the utility company as much as five hundred thousand dollars per day, and a reactor shutdown for replacement of a large stainless steel pipe section may take a week to ten days, including the time required for cooldown of the reactor and piping systems, removal of insulation surrounding the pipe section, replacement of the suspected pipe section and restarting of the reactor. Sometimes an after-the-fact examination of the "defective" pipe section shows that a critical IGSCC condition was not present and the power plant could have continued operating safely until a planned shutdown period.

Because of the difficulties in making accurate assessments of IGSCC conditions in power plant piping systems, research has been directed toward identifying features of ultrasonic return signals which might be utilized to distinguish return signals from geometric reflectors from return signals from IGSCC cracking conditions. Such research has generally utilized high speed analog to digital converters for converting the ultrasonic return signal into digital signal information stored in computer memory storage for subsequent processing through a general purpose computer system programmed to analyze various frequency and waveform features of the return signals. While such research was generally successful in identifying various return signal feature measurements which could be utilized together with a decision algorithm to distinguish IGSCC conditions from geometric reflectors, it was recognized that the cost and cumbersome nature of digital signal processing equipment was prohibitive from the standpoint of applying this method to in-service examination of power plant components.

Accordingly, it is the principal object of this invention to provide an improved system for analyzing output signals from an ultrasonic test instrument which can be utilized under field testing conditions.

More specifically, it is an object of this invention to provide an improved system for in-service detection of IGSCC conditions in sections of power plant piping systems.

It is another object of this invention to provide an analog circuit for measuring the partial amount of signal power in a preselected band of the frequency spectrum of an ultrasonic return signal.

It is another object of this invention to provide an improved analog/digital circuit for measuring features of the waveform of an ultrasonic return signal.

It is another object of this invention to provide an improved system and method for analyzing the output signals from an ultrasonic test instrument to distinguish the existence of IGSCC cracking conditions in power plant piping systems.

One aspect of this invention features a system for analyzing output signals from an ultrasonic test instrument representing ultrasonic return signals characterizing a structure being examined. This system includes partial power circuit means for measuring the partial amount of signal power in at least a first preselected band of the frequency spectrum of the return signal for producing a corresponding first partial power band signal. This system further includes waveform circuit means for measuring at least one preselected feature of the waveform of the return signal to produce a corresponding waveform feature signal. A combining circuit means is utilized for performing a preselected algorithmic combination of the first partial power band signal and the waveform feature signal to produce a test statistic signal. The test statistic signal is analyzed in decision circuit means to register a decision on a characteristic of the structure based on the value of the test statistic signal.

Preferably the partial power circuit means in the system includes a power band circuit means for measuring the amount of signal power in a preselectable band of the frequency spectrum of the return signal to produce a measured power band signal corresponding thereto, a total power circuit means for measuring the total signal power in the return signal and producing a total power signal corresponding thereto, and a divider circuit means for dividing the measured band power signal by the total power signal to produce the partial power band signal.

A preferred embodiment of the invention directed to the detection of IGSCC conditions utilizes a partial power circuit means which measures the partial amount of signal power in two preselected bands of the frequency spectrum of the return signal. This is accomplished by utilizing a second power band circuit means for measuring the amount of signal power in the second preselectable band of the frequency spectrum and dividing the second measured power band signal by the total power signal in a second divider circuit to produce a second partial power band signal.

Generally, the power band circuit means which measure the signal power in a partial band of the frequency spectrum include a filter circuit means for isolating the signal information in the preselected frequency band, an envelope circuit means for detecting the envelope of the filtered output signal, a squaring circuit means for squaring the detected envelope, and an integrating circuit means for integrating the squared envelope of the filtered output signal. To improve the accuracy of the partial power band measurement the preferred embodiment includes a single sideband frequency converter for converting the return signal to an upconverted return signal occupying a frequency band at least several times higher than the frequency band of the original return signal. Correspondingly, in the filter circuit means a frequency converter and tunable oscillator are provided for down-converting the up-converted return signal to a frequency band such that the center frequency of the partial power band to be measured is converted to a preselected lower frequency. At the output of the frequency down-converter, a bandpass filter having center frequency at this preselected lower frequency and a preselected bandwidth corresponding to the width of the power band to be measured is provided. In this manner, the isolation of the signal frequency bands whose power is to be measured is accomplished by tuning the frequency band position of the signal with respect to a fixed bandpass filter characteristic instead of attempting to tune the bandpass filter to the desired frequency of the power band to be measured.

A preferred embodiment of the invention also utilizes a normalizing circuit means receiving the original ultrasonic return signal for producing a normalized return signal having a fixed peak signal level. In this embodiment the waveform circuit means may include an envelope circuit means for detecting the envelope of the normalized return signal and may utilize a pair of signal comparator circuits for respectively signaling when the envelope signal exceeds a preselected threshold level and a preselected peak signal level. The preferred waveform circuit means also includes clock circuit means for generating clock pulses, rise time circuit means for counting clock pulses occurring during the transition of the envelope signal between the threshold level and the peak signal level, and duration circuit means for counting clock pulses occurring during the period of the output signal from the first comparator circuit. In the preferred embodiment directed to distinguishing IGSCC cracking conditions, the digital rise time and duration time signals are converted to analog signal values and the combining circuit means performs an analog algorithmic combination of the partial power band signals and the two waveform feature signals that produce tne test statistic signal to be processed in the decision circuit which registers, based on preselected decision criteria, whether the test statistic signal value corresponds to an IGSCC cracking condition.

Another aspect of this invention features a method of analyzing ultrasonic return signals characterizing a structure being examined which includes measuring in an analog manner the partial amount of signal power in at least a first preselected band of the frequency spectrum of the return signal and measuring in a digital manner at least one preselected feature of the waveform of the return signal. The method further includes converting the digital waveform feature measurement to a corresponding analog waveform feature value and combining the analog partial signal power measurement with the analog waveform feature value in accordance with a preselected algorithm to produce a test statistic. The method further includes registering a decision on the characteristic of the structure on the basis of the value of the test statistic. In a preferred method according to the invention, the ultrasonic return signal is normalized to a fixed peak signal level and frequency converted to a frequency band at a position at least several times higher than the position of the original return signal. A pair of partial frequency bands are isolated by separately converting the up-converted return signal down to two separate frequency bands such that the center frequency of each of two preselected partial bands of the original return signal is located at a preselected lower frequency point and then separately filtering the frequency down-converted return signals to isolate the signal information in the preselected partial frequency bands. Then to produce partial band power values the envelopes of the normalized return signal and the band filtered, down-converted return signals are separately detected, then separately squared and integrated, and finally the squared and integrated partial band signal envelopes are divided by the squared and integrated total signal envelope. The rise time and the duration time of the detected total signal envelope are digitally measured to provide waveform feature measurements and these digital measurements are then converted to analog values. The partial signal power values and the analog values of the duration time and rise time measurements are then combined in accordance with a preselected algorithm to produce a test statistic and a decision on a characteristic of the structure being examined is registered on the basis of the test statistic.

The apparatus and method of this invention has the advantage of providing an effective but relatively inexpensive approach to analyzing ultrasonic return signals. As applied to the detection of IGSCC cracking conditions, the system and method of this invention enables a sophisticated analysis of ultrasonic return signals from a pipe section to assist in making a determination of the presence of an IGSCC condition. The system of this invention can readily be packaged in a portable instrument case so that enhanced ultrasonic return signal analysis may be utilized in conjunction with in-service testing of structural components of a power plant or the like. The instrument and method of this invention should substantially enhance the capability of UT techniques to detect IGSCC conditions and may lead to accepted methods of sizing IGSCC flaws as part of a component replacement decision.

Other features and advantages of this invention will be apparent from a consideration of the detailed description given below in conjunction with the accompanying drawings.

FIG. 1 is a block schematic diagram of an ultrasonic test setup including apparatus in accordance with this invention and apparatus for carrying out the method of this invention.

FIG. 2 is a graph of an ultrasonic return signal waveform useful in explaining the apparatus and method of this invention.

FIG. 3 is a graph of the power versus frequency spectrum of an ultrasonic return signal useful in explaining the apparatus and method of this invention.

FIGS. 5A to 5E are circuit diagrams of an ultrasonic return signal measuring instrument in accordance with this instrument and FIG. 5F shows how the respective sheets of FIGS. 5A to 5E may be put together in an overall system diagram.

FIGS. 6A and 6B are signal timing diagrams useful in explaining a portion of the ultrasonic return signal measuring instrument in accordance with this invention.

Figure 4:
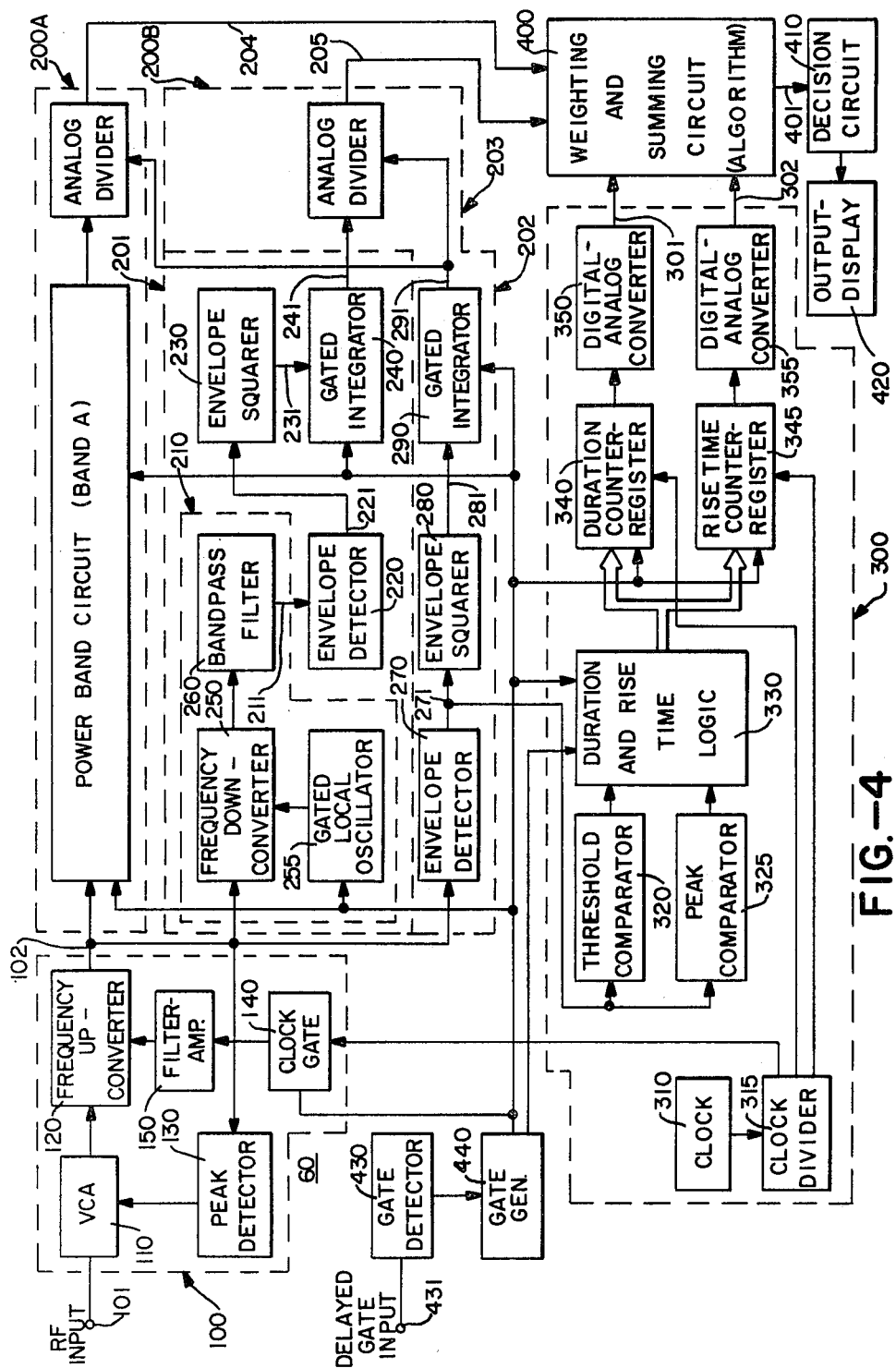
FIG. 4 is a block schematic diagram of a preferred embodiment of an ultrasonic return signal measuring instrument in accordance with this invention.

The apparatus depicted in FIG. 1 illustrates an ultrasonic test setup in accordance with this invention for detecting cracks in an in-service pipe section of a power plant. For purposes of illustration, the test setup of FIG. 1 will be considered to be directed toward the detection of IGSCC conditions in a nuclear power plant pipe section, but it should be understood that the return signal measuring instrument of this invention may be used in other types of structural testing environments. For purposes of use of the instrument of this invention in connection with detecting IGSCC conditions, the calibration concepts which are discussed in the copending Lapides patent application Ser. No. 206,627 filed Nov. 13, 1980 may be utilized and these concepts are hereby incorporated by reference into this application.

used in conventional, manual UT investigations. These conventional items are a transducer assembly 20, a transducer interface circuit 30, a UT instrument 40, and an oscilloscope display 50. Transducer assembly 20 includes a coupling block 21 and transducer 22. A viscous liquid couplant 25 such as mineral oil is provided for low impedance coupling of the ultrasonic signal into and out of the body of the item being tested, such as the in-service pipe section 70. The ultrasonic instrument 40 conventionally includes a pulser 41 and a receiver 42. The output signals from the conventional UT instrument 40 are typically a trigger output 41 which occurs on the leading edge of each ultrasonic pulse out of pulser 41, a radio frequency (RF) output signal representing the ultrasonic return signal, and a delayed gate signal on output 43 which is generated by the receiver and may be utilized to select a segment of the return signal time base for analysis.

A conventional, manual UT investigation starts with a calibration of this instrumentation utilizing a calibration block as explained in the above-referenced Lapides application. In addition to this convention calibration, the measuring instrument of this invention may utilize the algorithm tuning type calibration which is set forth in the above-referenced copending Lapides application. The return signal analyzing instrument 60 provided in accordance with this invention is utilized to implement a return signal waveform analysis based on a preselection of certain return signal features whose values are combined in accordance with a decision algorithm to produce an indication of whether the return signal corresponds to a cracking condition or some geometric reflector within the pipe section 70 under test. As indicated in the above-referenced Lapides application, the return signal measuring instrument may be calibrated either to simply detect cracking conditions or to discriminate between critical and subcritical cracking conditions. In general, once the algorithm of the measuring instrument has been set for performing a particular type of measurement, the transducer assembly 20 is placed on the in-service pipe section 70 so that the return signals from the pipe section may be analyzed by the measuring instrument 60. As will later be seen the setup of the instrumentation in accordance with this invention, the inspector will generally utilize the oscilloscope display as a way of identifying what segment of the ultrasonic return signal the measuring instrument will analyze so that the measurement will be specific to a selected time segment of the overall return signal waveform. The manner of making these selections and adjustments will be given in detail later.

The exemplary return signal analyzing instrument 60 according to this invention is directed to analyzing a plurality of ultrasonic return signal features whose values have been previously identified as being useful in distinguishing return signals from a IGSCC cracking condition and from geometric reflectors in the pipe section under study. The selection of the return signals to be measured was carried out by performing extensive ultrasonic examination studies of a number of pipe samples having a variety of known geometric reflectors and known cracking conditions. These ultrasonic examination studies were carried out by digitizing return signal information using a high speed analog to digital converter and storing the digitized signal information in a digital data storage apparatus such as a magnetic disk for use in a computer analysis of which waveform features and what type of decision algorithm would produce a high degree of discrimination of return signals from cracking conditions and geometric reflectors. One specific approach to conducting these ultrasonic examination studies and selecting ultrasonic return signal features for measurement is set forth in Technical Report R79-EPRI-1 entitled "Manual Analog Call Confirmer Design, Development, and Test" dated December 1979 which is available from Electric Power Research Institute, Inc., Palo Alto, California. The material in this report relating to the selection of ultrasonic return signal features for distinguishing return signals from cracking conditions and from geometric reflectors is hereby specifically incorporated herein by reference.

FIGS. 2 and 3 illustrate four examples of return signal features which may be used in distinguishing cracking conditions from geometric reflectors and which are implemented in the return signal analyzing instrument 60. FIG. 3 shows a typical return signal waveform section plotted in terms of signal amplitude versus time. For purposes of illustration, the pulse envelope of the return signal is indicated by the dashed curve on FIG. 3. As discussed in the above-mentioned Technical Report, two return signal features which have been identified to be of significant value in distinguishing cracking conditions in geometric reflectors are the pulse envelope rise time (RT) and the pulse envelope duration time (DT) which are labeled on FIG. 2. As will later be seen, the rise time is defined as the time required for the pulse envelope to make the transition between a preselected threshold level (e.g., 20% of peak) and a preselected peak level (e.g., 90% of absolute peak). Correspondingly, the duration time of the waveform is defined as the period during which the waveform envelope exceeds the preselected threshold level. As will later be seen, the preferred embodiment of this invention includes a digital measurement logic which is capable of handling various types of pulse envelope waveform shapes occurring within the gate period of the instrument, including envelopes which may have two peak regions which may or may not be associated with distinct return signal pulses.

FIG. 3 depicts a graph of the return signal frequency spectrum showing the power level in the return signal at various frequencies. Again, as set forth in the above-referenced Technical Report, two return signal features which have been determined to be useful in distinguishing signals from cracking conditions and from geometric reflectors are the percentage of return signal power in a pair of adjacent power bands of the frequency spectrum each having a width of 0.5 megahertz. For purposes of illustrating a specific embodiment of the return signal measuring instrument of this invention, an ultrasonic test instrument utilizing a transducer having a center frequency at 1.5 megahertz and producing output signals occupying the band from 0.5 to 2.5 megahertz will be utilized. For this type of transducer it has been ascertained that partial power band measurements in the 1.5 to 2 megahertz band and the 2 to 2.5 megahertz band are useful features for return signal discrimination.

In general, the selection of the partial band will depend on the operating frequency of the ultrasonic transducer and may also depend on the type of structure being analyzed and/or a type of structural defect to which signal discrimination is directed. Accordingly, the return signal analyzing instrument 60 in accordance with this invention has the capability of tuning the location of the partial power band frequencies which are to be measured.

FIG. 4 illustrates in block diagram form the main components of an ultrasonic return signal analyzing instrument in accordance with this invention. These main components are a signal normalizing circuit 100, a pair of partial power circuits 200A and 200B, a waveform circuit 300, a combining circuit 400, and a decision circuit 410. Normalizing and up-converting circuit 100 receives the input RF signal representing the ultrasonic return signal and produces a normalized up-converted return signal output on terminal 102. As will later be seen, the portion of the return signal on terminal 101 which is utilized for peak signal normalization is determined by the setting of the delayed gate in signal on input terminal 431 to gate detector 430 and the output gate pulse from gate signal generator 440. Each of the partial power circuits 200A and 200B measures the partial amount of signal power in a preselected band of the frequency spectrum of the return signal and produces a corresponding partial power band signal on outputs 204 and 205, respectively. Waveform circuit 300 measures preselected features of the waveform of the return signal and produces corresponding waveform feature signals on outputs 301 and 302. In this case the waveform circuit 300 measures both rise time and duration time of the return signal and produces a waveform duration signal on output 301 and a waveform rise time signal on output 302. Combining circuit 400 performs a preselected algorithmic combination of the partial power band input signals and the waveform feature input signals to produce a test statistic signal on output 401. Decision circuit 410 contains decision logic and registers a decision on a characteristic of the structure being analyzed based on the value of the test statistic signal. This signal may then be displayed in an output display 420 or otherwise indicated to the operator of the instrument.

As can be seen in FIG. 4, each of the partial power circuits includes a power band circuit 201 which measures the amount of signal power in a preselectable band of the frequency spectrum of the return signal and produces a measured band power signal on output lead 241. Partial power circuit 200B also includes, in common with partial power circuit 200A, a total power circuit 202 which measures the total signal power in the return signal and produces a total power signal on output lead 291. In addition partial power circuit 200B includes a divider circuit 203 for dividing the measured band power signal on output 241 by the total power signal on output 291 to produce the partial power band signal on lead 205. Partial power circuit 200A has the same circuits except for the shared total power circuit.

Power band circuit 201 includes a filter circuit 210, an envelope detector circuit 220, an envelope squaring circuit 230, and a integrating circuit 240. Filter circuit 210 produces a filter output signal on lead 211 which contains signal information in a preselected frequency band of the input ultrasonic return signal. Envelope circuit 220 detects the envelope of the filter output signal and produces a band envelope signal on lead 221. Envelope squaring circuit 230 squares the band envelope signal (in the mathematical sense of raising its signal amplitude to the power 2 or multiplying the signal amplitude by itself).

Accordingly, the output on lead 231 is a squared version of the band envelope signal on lead 221. This operation is performed since the power in the band is proportional to the square of the amplitude of the envelope which represents signal voltage. Integrator circuit 240 integrates the squared partial band envelope signal to produce the measured partial band power signal on output lead 241.

Total power circuit 202 includes envelope circuit 270 for detecting the envelope of the total return signal to produce a total envelope signal on lead 271. Envelope squaring circuit 280 squares the total envelope signal and produces a corresponding squared total envelope signal on output lead 281. Integrator circuit 290 integrates the squared total envelope signal to produce the total power signal on lead 291.

In the preferred embodiment of the return signal analyzing instrument depicted in FIG. 4 normalizing circuit 100 includes a single sideband frequency up-converter 120 which converts the input return signal on terminal 101 to an up-converted return signal on output lead 102 which is also normalized to a fixed peak signal level. The up-converted return signal occupies a frequency band at least several times higher than the frequency band of the original return signal. Rather than simply use a tunable bandpass filter as filter circuit 210 to tune the location and width of the bandpass filter to the power band to be measured, the instrument of this invention utilizes the approach of moving the frequency band of the return signal into the window of a fixed bandpass filter. Accordingly, filter circuit 210 includes a frequency down-converter 250 combined with a local oscillator circuit 255 to convert the up-converted return signal on lead 102 to a frequency band such that the center frequency of the partial power band to be measured is converted to a preselected lower frequency. Bandpass filter 260 then is a fixed bandpass filter having a center frequency at the preselected lower frequency and a preselected band width corresponding to the width of the power band to be measured.

The waveform circuit 300 shares the envelope detector 270 in total power circuit 202 although of course it could be provided its own envelope detector as a basis for forming the envelope of the amplitude of the RF return signal input on lead 101. In addition, waveform circuit means includes a pair of signal comparator circuits 320 and 325 for respectively signalling when the envelope signal on lead 271 exceeds a preselected threshold level and a preselected peak signal level. A clock circuit including clock 310 and clock divider 315 generates clock pulses and provides them to a rise time circuit consisting of rise time counter-register 345 and digital to analog converter 355 and to a duration circuit consisting of duration counter-register 340 and digital to analog converter 350. Rise time circuit 345, 355 operates under the control of duration and rise time logic 330 to count the clock pulses occurring during the transition of the envelope signal between the threshold level and the peak signal level, which peak signal level may be set at a preselected percentage of the total peak signal input. Correspondingly, the threshold comparator may be set at a preselected percentage of the peak signal level for initiating a rise time measurement and for controlling the duration time measurement. Duration circuit 340, 350 counts the clock pulses occurring during the period that the ultrasonic return signal exceeds the threshold level. For purposes of providing analog input signals to the combining circuit 400 the rise time and duration time counts stored in the registers in circuits 340 and 345 respectively are converted to analog signals on leads 301 and 302 by digital to analog converters 350 and 355.

Normalizing circuit 100 includes a peak detector 130 which detects the peak signal level of the frequency up-converted signal on lead 102 and feeds it to a voltage controlled amplifier 110. This feedback control voltage normalizes the peak signal level of the frequency up-converted signal to a fixed level. As shown in FIG. 4, the gate generator 440 which produces a gate signal of selectable duration triggered by the delayed gate input from the pulser receiver of the ultrasonic test instrument provides an output to a number of the other circuits in the instrument. The purpose of this circuit is to gate the various circuits operations which are being performed on the ultrasonic return signal to synchronize them with the segment of the return signal which is desired to be analyzed by the instrument. The ultrasonic return signal may contain several definite returns from various aspects of the structure under investigation. The output of gate generator enables the circuitry to focus the measurements on a specific segment of the return signal so that a specific return signal can be analyzed. Accordingly, clock gate 140 in normalizing circuit 110 is gated by the output of gate generator 440 so that frequency up-conversion is only performed on a selected segment of the ultrasonic return signal. Correspondingly, local oscillator 255 in filter circuit 210 is gated so that frequency down-conversion is performed only on that same segment of the ultrasonic return signal. In addition, integrator circuits 240 and 290 are gated by the gate signal output so that the only signal power measured is that of the selected segment of the ultrasonic return signal. Finally, the duration and rise time logic circuit 330 utilizes the gate generator outputs as part of a more complicated logic arrangement which enables selective measurement of the highest peak signal in a gate period despite the presence of two separate signal pulses in the gate period. As will later be seen in a discussion of specific logic circuitry the gate generator output signals are utilized to insure that the duration and rise time counts that are made are performed on the highest peak in the window which is also the peak utilized in the peak detector of normalizing circuit 100 for normalizing the input signal to a fixed peak level.

The structure and operation of the preferred embodiment of an ultrasonic return signal analyzing instrument in accordance with this invention will be discussed in connection with the schematic diagrams shown in FIGS. 5A to 5E. The instrument shown in FIGS. 5A to 5E is designed to analyze electronic signals resulting from ultrasonic pulse testing of austenitic stainless steel pipes used in nuclear power generating plants using a transducer and UT instrument operating at a 2.5 kilohertz repetition rate with signals occupying a bandwidth of 0.5 to 2.5 megahertz. The RF input signal on terminal 101 is the return signal from the receiver of the UT instrument and corresponds to the pulses returned from the structure under examination. In the return signal may be several distinct or overlapping pulses representing reflection points in the structure being analyzed. The delayed gate input on terminal 431 is received from the pulser receiver delay gate output and occurs at a preselected frequency such as every four hundred microseconds, for example.

Referring to FIG. 5A the RF input signal on lead 101 is processed in an automatic gain control loop which includes a single sideband frequency up-converter 121. The automatic gain control loop involves detecting the peak of the frequency up-converted signal and comparing it to a fixed reference level for generating an automatic gain control signal. A voltage controlled attenuator 111 together with an IC amplifier 112 and a bi-polar transistor stage 113 constitute a voltage controlled amplifier for processing the RF input signal on terminal 101 to present it to frequency up-converter 121 which is a single sideband frequency converter. The output of frequency converter 121 is bandpass filtered in a series L-C circuit 122 and then split into two signal paths in a signal splitter 123. One of the signal paths is amplified in an IC amplifier 131 and applied to a Schottky diode circuit 132 for peak detection. The detected peak voltage is compared to a reference offset voltage in a differential amplifier 133 whose output is then lowpass filtered and fed back as a control voltage signal to the voltage controlled attenuator 111. The local oscillator signal for frequency converter 121 is provided by the gated 21.4 megahertz clock output of clock divider 315. Clock gate 140 provides the 21.4 megahertz clock input to filter circuit 150 only during the gate signal interval of the gate generator 440. The output of filter circuit 150 is a sine wave signal at a 21.4 megahertz frequency for driving the single sideband frequency converter 121.

Frequency converter 121 substitutes a higher frequency carrier for the carrier signal of the incoming RF return signal waveform. Accordingly, whereas the incoming pulse may have only five or six carrier cycles, the up-converted pulse waveform at the output leads 102A, 102B, and 102C will have over fifty carrier cycles with the same envelope. It would, of course, be possible to perform the peak detection and gain control signal feedback to the voltage controlled attenuator 111 on the original RF signal, but the use of the frequency up-converted signal enhances the accuracy of the peak detection and thus produces a more accurate signal normalization. In addition, a separate, gated local oscillator could be provided for the frequency up-converter 121 but the use of the gated clock from clock divider 315 provides the necessary local oscillator signal without the expense of a separate transistor oscillator. The frequency up-converted output signal from signal splitter 123 is also amplified in a field effect transistor amplifier 124 and then fed through a signal transformer 125 to a pair of signal splitters 126A and 126B whose outputs 102A–102C feed the power band circuit 201 and the total power circuit 202 shown in FIG. 5B.

FIG. 5A also shows the delayed gate input signal on terminal 431 being detected by a gate detector circuit 430 to fire a one-shot multivibrator which serves as the gate signal generator 440. The width of the output pulse from the monostable multivibrator and thus the duration of the gate signal period is controlled by a front panel potentiometer 441. Preferably the gate output signal is connected into one channel of the oscilloscope display shown in FIG. 1 so that the position and duration of the gate signal with respect to the return signal pulses will be displayed. The complementary outputs of one shot multivibrator 440 on leads 442 and 443 are provided to several circuits in other portions of the instrument.

Clock circuit 310 produces an output clock signal at a 42.8 megahertz frequency which is supplied to clock divider 315. Clock divider 315 divides the 42.8 megahertz clock frequency to a 21.4 megahertz frequency to serve as the clock input to clock gate 140 and also provides a 4.28 megahertz clock and a 5.26 megahertz clock on output leads 316 and 317 which go to the duration counter and rise time counter, respectively, on FIG. 5E.

Figure 5C:
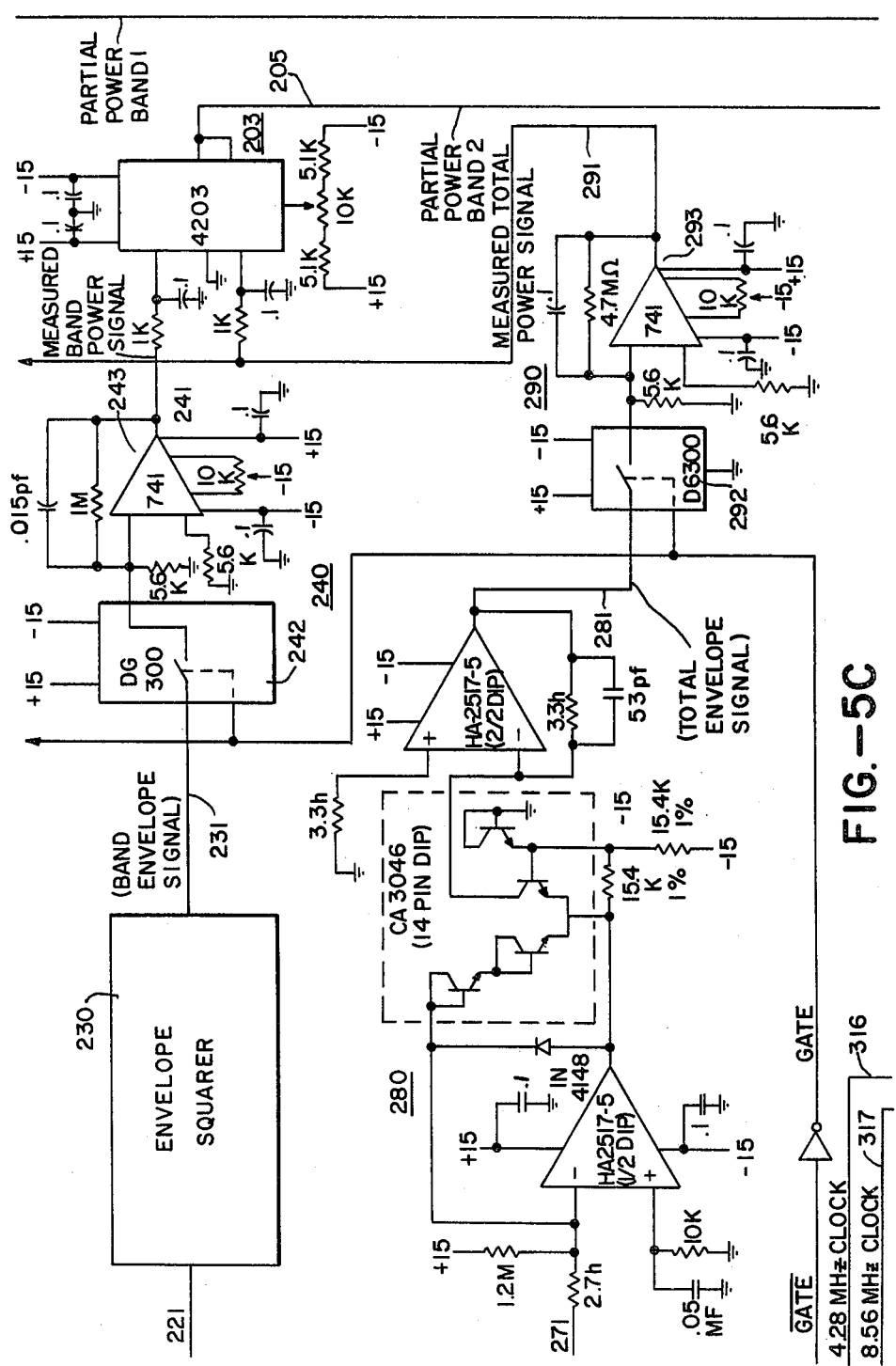

The frequency up-converted return signals on leads 102A and 102B are supplied to the filter circuits 210 in the partial power circuits which are depicted on FIGS. 5B and 5C. Only one of the partial power circuits is actually depicted since the same identical circuitry is employed for both. Accordingly, as shown in FIG. 5B the frequency up-converted signal on lead 102B is supplied to a frequency converter 250 which is driven by the output signal from gated local oscillator 255. Oscillator 255 is tunable by way of a tunable feedback capacitor 256 so that the center frequency of the power band whose power is to be measured is converted to eight megahertz. The input to this circuit has already undergone a lower sideband frequency conversion with a 21.4 megahertz signal so the tunable oscillator frequency $f_o$ is set according to the following equation:

$$21.4 - f_c - f_0 = 8,$$

where $f_c$ is the center frequency of the slot whose power is to be measured.

The output of frequency converter 250 is supplied to a three-stage L-C bandpass filter through an integrated circuit amplifier 252. The L-C bandpass filter 250 is designed to have a center frequency at eight megahertz and a 0.5 megahertz bandwidth. Accordingly, the output of bandpass filter 250 is a signal containing only frequency components within the passband of the filter. This filter output signal is supplied to envelope detector 220 which essentially comprises a first Schottky diode 222 which detects the envelope and a second Schottky diode 223 which compensates for the DC offset. The envelope detector output is amplified and lowpass filtered in an operational amplifier circuit 224 with a lowpass filter cutoff of one megahertz to produce a band envelope signal on lead 221.

As shown in FIG. 5B the frequency up-converted signal on lead 102C is supplied to envelope detector 270 which also consists of a first Schottky diode 272 which detects the envelope of the frequency up-converted signal and a second Schottky diode 273 which provides DC offset compensation. The detected envelope signal is amplified and lowpass filtered in a pair of operational amplifier circuits 274 and 275 having a five megahertz cutoff frequency to produce a total envelope signal which is supplied to the waveform feature circuit 300 shown in FIGS. 5D and 5E and to the remainder of the total power circuit 202 depicted on FIG. 5C.

As shown in FIG. 5C, the band envelope signal on lead 221 is supplied to envelope squaring circuit 230 and the total envelope signal on lead 271 is supplied to envelope squaring circuit 280. Since the two squaring circuits 230 and 280 have the same circuit structure only one is shown in detail in FIG. 5C. The output of envelope squaring circuit 230 is a squared version of the band envelope signal and the output of envelope squarer 280 on lead 281 is the total envelope signal squared.

The squared band envelope signal on lead 231 is supplied to a gated integrator circuit 240 which consists of a digital gate 242 and an operational amplifier integrator circuit 243. Digital gate 242 is controlled by the gate signal from gate generator 440 on FIG. 5A so that the squared band envelope signal presented to the digital gate is coupled to the input of integrator 243 only during the period of the gate signal. The integrator 243 has a lowpass filtering characteristic with a time constant equal to about thirty pulses so that after about thirty input pulses of the ultrasonic return waveform have been processed, the output on lead 241 comprising the measured band power signal stabilizes at an average voltage level corresponding to the average signal power in the measured band.

The squared total envelope signal on lead 281 is fed to gated integrator 290 which consists of a digital gate 292 and an operational amplifier circuit 293 in an integrating lowpass filter configuration. Digital gate 292 is also operated by the gate output of gate generator 440 on FIG. 5A so that the squared total envelope signal is presented to the integrating amplifier 293 only during the period of the gate signal. The time constant of the integrator is such that the measured total power signal output on lead 291 builds up to an average total signal, power value after about thirty pulses.

The measured band power signal on lead 241 is supplied along with the measured total power signal on lead 291 to analog divider circuit 203 where the measured band power signal is divided by the measured total power signal to produce the partial power band signal on lead 205.

As shown in FIG. 5D, the total envelope signal on lead 271 is provided to a threshold comparator circuit 320 and a peak comparator circuit 325. The threshold comparator output signal (THR) on lead 321 and the peak comparator output signal (PEAK) on 326 are supplied along with the GATE signal on lead 442 and the $\overline{\text{GATE}}$ signal on lead 443 to duration and rise time logic circuit 330. This duration and rise time logic circuit 330 provides the necessary control signals for proper operation of the duration counter-register circuit 340 and the rise time counter-register circuit 345 shown on FIG. 5E. The overall operation of this circuitry can best be seen by considering the signal waveform and logic timing charts shown in FIG. 6A.

Consider first an input waveform of the total envelope signal as shown in FIG. 6A. This input waveform simply constitutes a single pulse within the period of the GATE signal shown immediately below the total envelope signal. The GATE signal goes HIGH at time T1 due to detecting the delayed gate input in gate detector 430 on FIG. 5A and firing the one-shot multivibrator 440 which serves as gate generator 441. At this time the various signals shown in FIG. 6A have the logic levels indicated. At time T2 the total envelope signal has crossed the selected threshold of threshold comparator 320 (20% of peak in this case) so that the THR signal goes HIGH. When THR goes HIGH it enables the 4.28 megahertz clock pulses input in to flip-flop 343 to be gated into duration time counter 341. At this same time valid pulse latch 331 is in a reset condition with a HIGH output on its $\overline{\text{VP}}$ output lead which feeds NAND gate 332. Since the $\overline{\text{EOP}}$ input to NAND gate 332 is HIGH at this time and the THR signal input to NAND gate 332 is also HIGH at this time, NAND gate 332 will have a LOW output which is inverted by amplifier 332A to a HIGH output on the count rise time (C/RT) signal. This C/RT signal is coupled to a flip-flop 348 to provide a count enable signal to counter 346 which is synchronized by the 8.56 megahertz clock signal. Consequently, the 8.56 megahertz clock signals begin accumulating in counter 346.

At time T3 when the total envelope signal reaches the preselected peak level which is set at this case at 90% of the total normalized peak signal value, the PEAK signal on lead 326 from peak comparator 325 goes LOW. This negative going signal transition causes valid pulse latch 331 to set so that its output $\overline{\text{VP}}$ lead goes LOW and its VP lead goes HIGH. When $\overline{\text{VP}}$ goes LOW, the output of NAND gate 332 goes HIGH so that the C/RT signal goes LOW. This disables the further accumulation of 8.56 megahertz clock signals in rise time counter 346.

A short time later the total envelope signal recrosses the peak comparator level and the PEAK signal goes HIGH again but this does not change the state of valid pulse latch 331. However, at time T4 the total envelope signal has recrossed the threshold level so that the THR signal on lead 321 goes LOW. When THR goes LOW it causes valid pulse latch 331 to reset so that output $\overline{\text{VP}}$ goes HIGH and output VP goes LOW. When $\overline{\text{VP}}$ goes HIGH, it triggers end of pulse (EOP) one shot 333. Accordingly, the $\overline{\text{EOP}}$ lead goes HIGH and the EOP lead correspondingly goes LOW. These signals remain for the four hundred nanosecond interval of one shot 333. At the time EOP goes HIGH, the pulse counter flip-flop 334 is in a reset condition so that the P2 lead is LOW and the $\overline{\text{P2}}$ lead is HIGH. With both EOP and $\overline{\text{P2}}$ HIGH, NAND gate 333A is enabled and its output goes LOW. Accordingly, the output of NOR gate 333B goes HIGH and the register clock (REG. CL.) lead goes LOW due to the inverting amplifier 333C. Thus at time T4, when THR goes LOW, the duration time counter 341 is disabled because flip-flop 343 resets on the next clock pulse. As the REG. CL. lead goes LOW the counts stored in the duration time counter 341 and the rise time counter 346 are clocked into registers 342 and 347, respectively. Thus at time T4 the counted duration time and rise time clock pulses are entered into registers 342 and 347 and presented to digital to analog converters 350 and 355. The outputs of digital to analog converters 350 and 355 on leads 351 and 356 will be analog signal voltages of magnitude corresponding to the duration time and rise time counts.

At time T5 when the end of pulse one shot times out, EOP goes LOW and correspondingly $\overline{\text{EOP}}$ goes HIGH. When $\overline{\text{EOP}}$ goes HIGH, it triggers LOAD one shot 348A to produce a 300 nanosecond output LOAD pulse which loads both duration time counter 341 and rise time counter 346 with preset all zero count. Also at time T5, as $\overline{\text{EOP}}$ goes HIGH pulse counter 334 is clocked to a set state with P2 going HIGH at this time and $\overline{\text{P2}}$ going LOW. Since, however, there is no second pulse in the window of the GATE signal nothing further happens until at time T6 when the GATE signal goes LOW and resets the pulse counter 334 so that $\overline{\text{P2}}$ goes LOW. Also since there was only one pulse in the window the other logic circuitry does not come into play.

Summarizing then, between time T2 and T3 when the total envelope signal is in its rise time period between the threshold level and the peak level, 8.56 megahertz clock pulses are counted in counter 346 but that accumulation is stopped at time T3 as the C/RT signal goes LOW when the peak comparator is triggered and resets the valid pulse latch 331. The duration clock pulses at 4.28 megahertz are counted throughout the interval of the THR signal being HIGH which is between time T2 and T4. At time T4 the end of pulse one shot is fired which causes the counter outputs to be clocked into the registers by the REG. CL. signal, and a short time later at T5 the counters are loaded with the preset zeros. The registered duration and rise time counts in registers 342 and 347 are presented to the combining circuit as analog signals through the action of the digital to analog converters 350 and 355. The registers 342 and 347 will retain the duration time and rise time count measurement until a new value is clocked into the registers which will not occur until about four hundred microseconds later when another pulse comes along in the window. Assuming the next pulse is identical with the former, the measurement will stay the same. If the transducer has been moved, so the return signal changes, the measurements will change accordingly.

FIG. 6B shows a pulse waveform and logic timing diagram for the case where two pulses appear in the window of the GATE signal on lead 442. In the case shown in FIG. 6B pulse 1 has a lower peak amplitude than pulse 2 and the pulses are considered distinct because the envelope signal of pulse 1 recrosses the threshold level before rising again to form pulse 2. This is the definition of two distinct pulses in this case since pulse number 1 must recross the threshold in order to clock the pulse counter 334 to a set state. As will later be seen, this is the condition for bringing into play the circuitry involving analog gate 335B, peak sample and hold circuit 335 and peak comparator 335A which compare the peak amplitudes of two distinct pulses in the window of the gate pulse to determine which of the separate rise time and duration time measurements on the individual pulses will be utilized and sent to the combining circuit 400.

Generally the comparators and logic circuit operate on pulse number 1 in FIG. 6B in essentially the same fashion that they operated on the pulse in FIG. 6A and thus it is unnecessary to repeat that description here. Consider, however, the operation now of the peak sample and hold circuit 335 and the peak comparator circuit 335A. Between times T1 and T5, pulse counter 334 is in a reset condition so that $\overline{P2}$ is HIGH. At this time the $\overline{GATE}$ signal is LOW. With $\overline{P2}$ HIGH, analog gate 335B provides a closed signal path for the pulse envelope signal so that the peak amplitude of pulse number 1 will be stored on the capacitor in the sample and hold circuit 335. During this period the $\overline{GATE}$ signal holds the other signal path to ground open so that the capacitor can charge to the peak signal level of pulse number 1. At time T5 when P2 goes HIGH and $\overline{P2}$ goes LOW, analog gate 335B opens the path from the total envelope signal input to the peak holding circuit so that no further change in the peak voltage stored on the capacitor can occur. Consequently, the input to the peak signal comparator 335A remains the stored peak level of pulse number 1. At time T4 the rise time and duration time counts from pulse number 1 had been entered into the registers 342 and 347 by the REG. CL. signal going LOW. However, at time T5 the counters 341 and 346 for duration time and rise time have been loaded to all zeros. Accordingly, at time T6 when THR goes HIGH again as the threshold level is crossed by the envelope of pulse number 2, a new duration time and rise time count begins to accumulate in counters 341 and 346. These newly accumulating duration time and rise time values do not affect the information stored in the registers 342 and 347.

At time T7 the rise time count has been completed as the pulse 2 envelope signal crosses the peak comparator level and at time T8 the P2H output of the peak comparator 335A goes HIGH as the envelope signal of pulse number 2 exceeds the peak level of the envelope of pulse number 1. When P2H goes HIGH, it sets pulse comparator latch 336 since the inputs to NAND gate 336A are all HIGH at this time so that its output goes LOW. That is to say the P2 input to NAND gate 336A is HIGH because the pulse counter flip-flop is in a set condition (pulse two state) caused by the timing out of the end of pulse one shot 333 at time T5, and the VP signal is HIGH since the valid pulse latch 331 has been set at time T7 when the envelope signal of pulse 2 cross the peak comparator level. With the pulse comparator latch 336 now set so that its output P2H/L is HIGH, at time T9 when another EOP signal is generated by end of pulse one shot 333 because the envelope signal of pulse 2 has recrossed the threshold comparator level to reset the valid pulse latch 331, another REG. CL. signal is generated. This is caused by the EOP input to NAND gate 336A going HIGH at time T9 while the P2H/L input is also HIGH. The corresponding LOW output of NAND gate 336A causes the output of NAND gate 333B to go HIGH and the output of the inverting amplifier 333C to go LOW producing the REG. CL. pulse. The REG. CL. pulse causes the new rise time and duration time counts accumulated in counters 341 and 346 to be clocked into registers 342 and 347 for presentation to the associated digital to analog converters so that corresponding analog values are sent to the combining circuit 400. Thus, in effect the duration time and rise time count for pulse number 1 has been thrown away and the new duration time and rise time count for pulse number 2 becomes effective and the measurements for pulse 2 remain effective for the four hundred microsecond interval between pulses.

At time T10 a new load pulse is generated by the load one shot 348A so that the counters are again loaded to a preset zero count. At time T11 when the gate signal goes LOW, the pulse comparator latch 336 is reset. Also at this time the $\overline{GATE}$ signal goes HIGH so that the ground path to the capacitor in the peak storage circuit 335 is established to rapidly discharge the capacitor for the next peak sample and hold operation. The end of the gate signal also resets the pulse count flip-flop 334 so that it is ready to process the next pulse as pulse number 1.

Consider now from the general operation depicted in FIG. 6B what would happen if the second pulse were of lower peak amplitude than the first pulse. It should be apparent that under these conditions the logic circuitry will cause the rise time and duration time counters to count the rise time and duration time of the second pulse but no new REG. CL. signal will be generated. This is due to the fact that the P2H signal at the output of the peak comparator 335A will remain LOW since the second peak is lower than the first. Correspondingly, the peak comparator latch 336 will not be set so that, when the second end of pulse signal occurs at time T9, NAND gate 336A is not enabled so that the second REG. CL. signal will not be produced. Accordingly, the rise time and duration time measurements on the second pulse are thrown away when the second load signal comes along at time T10 to load the counters to preset zero state. The count stored in the register retains the rise time and duration time measurements of the first pulse which continue to be presented to the combining circuit 400 through the digital to analog converters throughout the interval between pulses.

Consider now the condition where two non-distinct signal pulses occur in the window, i.e., the first pulse does not recross the threshold level but simply dips between peaks. For this case the rise time measurement will be made between the traversing of the envelope signal between the threshold comparator level and the peak comparator level and the duration time measurement will be made for the total length of the time that the envelope signal is above the threshold comparator level. Since the envelope of the pulse does not recross the threshold before reaching a new peak, no end of pulse signal is generated until the threshold level is finally crossed after the second peak in the envelope signal occurs. Consequently, only one end of pulse signal is generated. The peak comparison circuit does not enter into the picture under these conditions because the pulse counter flip-flop 334 is not set until the end of pulse signal has been generated after the second peak has occurred.

From the above discussion it should be apparent that the instrument can be set up to measure the smaller of two pulses that are side by side simply by programming the gate generator one shot 440 in FIG. 5A to have a period such that the gate signal terminate after the smaller pulse and before the larger pulse occurs. Similarly, a smaller pulse occurring after a large pulse can be measured by causing the delayed gate signal input to the gate detector 430 on FIG. 5A from the pulser receiver to occur between the two pulses. In this manner the gate signal will be generated only after the first larger pulse has occurred and the measurements will be made only on the second and smaller pulse. It should also be understood that under these conditions the other measurements being made will be only on the smaller pulse as well since the gate signal will be HIGH only during the smaller pulse and the other circuitry which is gated by that signal will only be active during the period of the second pulse. The peak signal normalization will be operating on the second pulse so that the second pulse amplitude will be normalized to a fixed peak level for the rise time and duration time measurements.

Figure 5E:
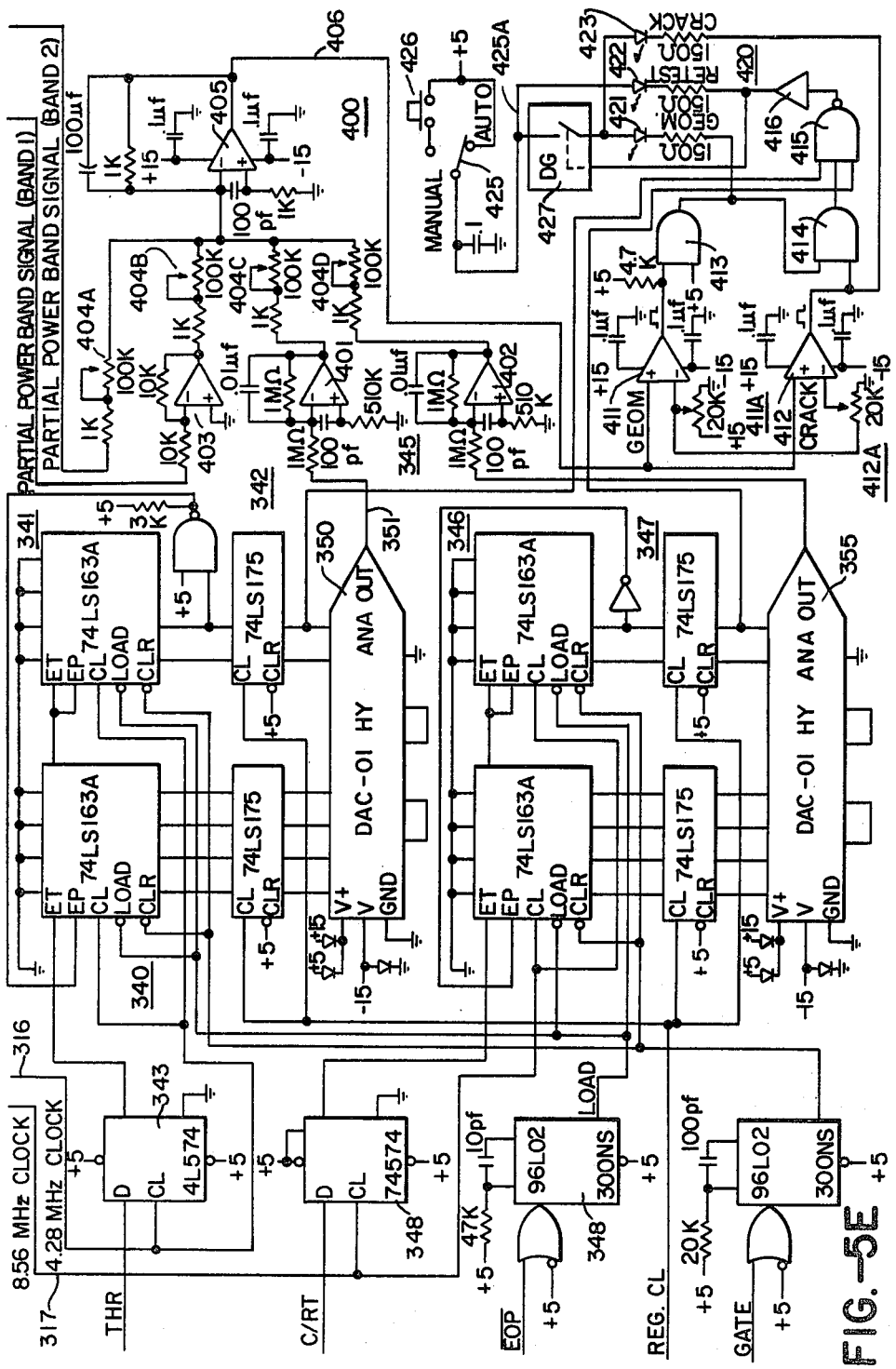

Consider now the operation of the combining circuit 400. Combining circuit 400 is, as shown in FIG. 5E, a weighting and summing circuit which linearly sums the weighted versions of the analog partial power band signals from band 1 and band 2 and the analog waveform duration time and waveform rise time signals from the digital to analog converters 350 and 355. As previously mentioned, each of these signals is a relatively steady DC voltage due to the lowpass filter time constant in the partial power band measurement circuits. In addition, the outputs of the digital to analog converters 350 and 355 are processed through a lowpass filter type differential amplifier circuits 401 and 402 to smooth the output of the digital to analog converters. Due to the selection of the algorithm to be implemented in the weighting and summing circuit 400 the partial power band signal from band 1 is inverted in a unity gain inverting amplifier 403 as part of the weighting and summing operation. The potentiometers 404A–404D perform the weighting operation on the four analog input feature signals and the operational amplifier 405 sums the weighted versions of the feature measurement signals to produce a test statistic signal on output lead 406.

Decision circuit 410 consists of a pair of differential amplifiers 411 and 412 which individually operate to compare the test statistic signal on lead 406 with a pair of decision threshold values set by potentiometers 411A and 412A respectively. In the circuitry shown in FIG. 5E the decision circuit is set up to implement a differentiation between return signals from IGSCC cracking conditions and from geometric reflectors with a retest indication being given if the test statistic signal falls between the crack threshold and the geometry threshold. Since the algorithm in the combining circuit is set such that the magnitude of the test statistic signal on lead 406 will be smaller for return signals from cracking conditions, the crack decision threshold is smaller than the geometry decision threshold.

Accordingly, the geometry threshold is set into potentiometer 411A and the lower crack threshold is set into potentiometer 412A. If the test statistic signal on lead 406A is below the crack threshold of potentiometer 412A then the outputs of both differential amplifiers 411 and 412 are LOW. With the output of differential amplifier 412 LOW, the light emitting diode 423 has a five volt signal across it when a five volt signal is applied to the opposite lead either through the AUTOswitch position of switch 425 or when the switch 425 is in the manual position and pushbutton switch 426 is pressed. Either of those conditions puts five volts on lead 425A. Digital gate 427 is closed at this time due to the output of inverter 416 being HIGH. The output of inverter 416 is HIGH due to the following chain of logic operation. NAND gate 413 has a LOW input from differential amplifier 411 and so has a HIGH output. The HIGH output from NAND 413 combines with the LOW output from differential amplifier 412 to produce a HIGH output from NAND gate 414. With NAND gate 414 output HIGH, all of the inputs to NAND gate 415 are HIGH, assuming that the most significant digit of registers 342 and 347 have a HIGH output due to the register not being full. Accordingly, NAND gate 415 has a LOW output which is inverted by amplifier 416 to a HIGH output. With digital gate 427 closed, plus five power supply voltage is applied to both diodes 421 and 422 and 423. However, diodes 421 and 422 have a HIGH signal condition on the opposite side of the diode so neither of them light. The LOW condition on the other side of diode 423 causes it to light indicating that the return signal is from a crack condition.

Consider now the situation when the test statistic signal on lead 406 exceeds the geometry threshold voltage set in potentiometer 411A. Under this condition both the differential amplifiers 411 and 412 will have a HIGH output. NAND gate 413 then has two HIGH inputs which causes its output to go LOW. This causes the geometry LED 421 to light (assuming digital gate 427 is closed) to apply five volts to the other side of diode 421. Since NAND gate 414 has HIGH and LOW inputs, its output will be HIGH. Again, assuming that registers 342 and 347 have not reached a full condition, NAND gate 415 will then have all HIGH outputs and thus a LOW output. The LOW output is inverted by inverting amplifier 416 to a HIGH input which closes digital gate 427. Accordingly, the HIGH signal on the lefthand side of LED's 422 and 423 buck the power supply voltage on the other side of those diodes to keep those diodes off and only the geometry diode 421 is lit.

Consider now the case where the test statistic signal falls between the crack threshold set in potentiometer 412A and the geometry threshold set in potentiometer 411A. Under this condition the output of differential amplifier 412 is HIGH and the output of differential amplifier 411 is LOW. NAND gate 413 has a LOW input so its output is HIGH. Accordingly, NAND gate 414 has two HIGH inputs producing a LOW output. A LOW output of NAND gate 414 causes NAND gate 415 to have a HIGH output which is inverted by inverting amplifier 416 to a LOW signal as supplied to light emitting diode 422. Also, the LOW output of amplifier 416 opens the digital gate 427 to remove five volts from the light emitting diodes 421 and 423 preventing them from operating. Accordingly, only the retest diode 422 is lit indicating that the analyzing instrument could not with confidence determine whether the return signal was from a crack or geometry.

The input signals from the most significant bit leads of registers 342 and 347 into NAND gate 415 are provided to cause a retest indication whenever the duration time or rise time measurements have reached or exceeded the capacity of the registers 342 or 347. In other words, if either one of these register capacities is reached the most significant bit output goes LOW, causing the output of NAND gate 415 to go HIGH which is inverted by inverting amplifier 416 to a LOW to cause the retest LED 422 to light.

The switch 425 enables the operator of the instrument to select the operating mode of the display 420. In the AUTO position the display is continuously active and one or the other of the LED's 421 to 423 will be lit at all times. This may be distracting when the operator is moving the transducer and causing the various LED's to flash on and off due to the changing return signal input to the instrument. In the manual position of switch 425, the display is inactive until pushbutton 426 is pressed. This enables the operator to disable the display until he has the transducer in the position which he desires to measure from, at which time he can activate the display by pushing the pushbutton 426.

The weighting and summing circuit 400 implements a Fisher linear discriminant type algorithm for the input return signal feature measurements. The Fisher discriminant F to be implemented is given by the following equation:

$$F = w_1 T_D + w_2 P_1 + w_3 P_2 + w_4 T_R$$

where $T_D$ is the duration time in microseconds, $P_1$ is the partial power band signal in band 1, $P_2$ is the partial power band signal in band 2, $T_R$ is the rise time in microseconds, and $w_1$ to $w_4$ are the weighting coefficients set in the potentiometers 404A through 404D. For the Fisher discriminant algorithm in this case the weighting factor for the partial power band signal $P_1$ (i.e., $w_2$) is negative and this is the reason for the unity gain inverting amplifier 403 at the input to potentiometer 404B.

The decision rule implemented by decision circuit 410 is given by the following table with the understanding that $\theta_G > \theta_C$:

| Decision | Condition |
|---|---|
| crack | $F < \theta_C$ |
| retest | $\theta_G > F > \theta_C$ |
| geometry | $F > \theta_G$ | where $\theta_C$ is the crack decision threshold set in potentiometer 411A and $\theta_G$ is the geometry decision threshold set into potentiometer 412A. It will of course be appreciated that the weighting potentiometers 404A through 404D must be set to take into account not only the weighting factors of the various measurements but the scale factors involved in the actual measuring circuitry. In addition, an overall scale factor has to be considered to maintain the test statistic signal within the dynamic constraints of the circuitry of the instrument. Specific instructions for carrying out the setup of the weighting potentiometer values for the discriminant function to be utilized in connection with IGSCC conditions is set forth in the above-referenced EPRI Technical Report and is hereby incorporated by reference.

It should be understood that the above description of an exemplary preferred embodiment of this invention with respect to detecting of IGSCC conditions is given by way of example only and numerous modifications could be made therein without departing from the scope of the invention. In particular, it should be understood that the algorithm implemented in the combining circuit and the decision logic could be set up to distinguish between cracking conditions of various magnitudes such as cracking conditions which are critical and require replacement of the structure under test versus those which are subcritical and do not require replacement. It should also be apparent that the apparatus for implementing the algorithm could be different from that disclosed above. For example, the algorithm could implement various combined analog and digital logic functions with either digital or analog weighting of the various feature measurements. Additional modifications other than the ones suggested above could also be implemented by persons of skill in this art.

It should also be understood that, although the description of the preferred embodiment relates to a particular test set up for detection of IGSCC conditions in stainless steel pipes the return signal analyzing instrument and the method which it implements could be utilized in other ultrasonic testing environments where return signal feature measurements would assist in making a decision as to the condition of the structure being examined.

What is claimed is:

1. In a system for analyzing output signals from an ultrasonic test instrument representing ultrasonic return signals characterizing a structure being examined,
   partial power circuit means for measuring the partial amount of signal power in at least a first preselected band of the frequency spectrum of said return signal and producing a corresponding first partial power band signal;
   waveform circuit means for measuring at least one preselected feature of the waveform of said return signal and producing a corresponding waveform feature signal;
   combining circuit means for performing a preselected algorithmic combination of said first partial power band signal and said waveform feature signal to produce a test statistic signal; and
   decision circuit means for registering a decision on a preselected characteristic of said structure based on the value of said test statistic signal; and algorithmic combination being preselected on the basis of experimental data demonstrating a substantial degree of discrimination in said test statistic signal value for said preselected characteristic of said structure.

2. The system of claim 1, wherein said partial power circuit means includes a power band circuit means for measuring the amount of signal power in a preselectable band of the frequency spectrum of said return signal and producing a measured band power signal corresponding thereto;

total power circuit means for measuring the total signal power in said return signal and producing a total power signal corresponding thereto;

divider circuit means for dividing said measured band power signal by said total power signal to produce said partial power band signal.

3. The system of claim 2, wherein said partial power circuit means includes a second power band circuit means for measuring the amount of signal power in a second preselectable band of the frequency spectrum of said return signal and producing a second measured band power signal corresponding thereto; and second divider circuit means for dividing said second measured band power signal by said total power signal to produce a second corresponding partial power band signal, and wherein said combining circuit means performs a preselected algorithmic combination of both said first and second partial power band signals and said waveform feature signal to produce said test statistic signal.

4. The system as claimed in any of claims 2 and 3, wherein each of said power band circuit means includes filter circuit means for producing a filter output signal containing signal information in said preselected frequency band, envelope circuit means for detecting the envelope of said filter output signal and producing a band envelope signal, envelope squaring means for squaring said band envelope signal and integrating circuit means for integrating said squared band envelope signal to produce said measured band power signal; and said total power circuit means includes envelope circuit means for detecting the envelope of said return signal and producing a total envelope signal, squaring circuit means for squaring said total envelope signal, and integrating circuit means for integrating said total envelope signal to produce said total power signal; and each of said divider circuit means is an analog signal divider receiving one of said measured band power signals and said total power signal for producing a corresponding partial power band signal.

5. The system of claim 4, further comprising a single sideband frequency converter for converting said return signal to an up-converted return signal occupying a frequency band at least several times higher than the frequency band of said return signal; each of said filter circuit means in said power band circuit means includes a frequency converter and tunable oscillator combination for converting said up-converted return signal to a frequency band such that the center frequency of the partial power band to be measured is converted to a preselected lower frequency and a bandpass filter having a center frequency at said preselected lower frequency and a preselected band width corresponding to the width of said power band to be measured.

6. The system of claim 1, further comprising normalizing circuit means receiving said ultrasonic return signals for producing a normalized return signal having a fixed peak signal level; and wherein said waveform circuit means includes envelope circuit means for detecting the envelope of said normalized return signals; at least a pair of signal comparator circuits for respectively signaling when said envelope signal exceeds a preselected threshold level and a preselected peak signal level; clock circuit means for generating clock pulses; rise time circuit means for counting clock pulses occurring during the transition of said envelope signal between said threshold level and said peak signal level; and duration circuit means for counting clock pulses occurring during the period of the output signal from said first comparator circuit.

7. In a system for analyzing output signals from an ultrasonic test instrument representing ultrasonic return signals characterizing a structure being examined, normalizing circuit means receiving said ultrasonic return signals for producing a normalized return signal having a fixed peak signal level;

first and second filter circuit means coupled to said normalizing circuit means for producing filtered output signals containing return signal information in first and second preselected frequency bands;

first, second, and third envelope circuit means individually coupled to said filter circuit means and to said normalizing circuit means for separately detecting the envelopes of said first and second filter output signals and said normalized return signal and producing first and second band envelope signals and a total envelope signal;

first, second, and third squaring circuit means individually coupled to said envelope circuit means for producing squared versions of said first and second band envelope signals and said total envelope signal;

first, second, and third integrator circuit means coupled individually to said squaring circuit means for integrating said squared versions of said first and second band envelope signals and said total envelope signal to produce first and second measured band power signals and a total power signal;

a pair of analog dividers coupled to said integrator circuit means for dividing each of said first and second measured power band signals by said total power signal to produce a first and second partial power band signals;

first and second signal comparator circuits for respectively signaling when said total signal envelope exceeds a preselected threshold level and a preselected peak signal level;

clock circuit means for generating clock pulses;

rise time circuit means for counting clock pulses occurring during the transition of said total envelope signal between said threshold level and said peak signal level and producing a stored rise time signal;

duration circuit means for counting clock pulses occurring during the period of the output signal from said first comparator circuit and producing a stored duration time signal;

first and second converter means for converting said stored rise time signal and said stored duration time signal to corresponding rise time and duration time analog signals;

combining circuit means coupled to said analog dividers and said converter circuit means for performing a preselected algorithmic combination of said first and second partial power band signals and said analog rise time and duration time signals to produce a test statistic signal; and decision circuit means for for registering a preselected characteristic of said structure based on the value of said test statistic signal; said algorithmic combination being preselected on the basis of experimental data demonstrating a substantial degree of discrimination in said test statistic signal value for said preselected characteristic of said structure.

8. The system of claim 7, adapted to be used with an ultrasonic test instrument which produces a delayed gate signal representing the period of the return signal to be analyzed and further including a gate detector circuit and a gate signal generator coupled to said gate detector circuit for generating a gate signal of selectable duration in response to said delayed gate signal; and said normalizing circuit means includes a single sideband frequency converter receiving said normalized return signal and oscillator signal means for supplying to said frequency converter a modified carrier signal of preselected frequency during said gate signal duration to produce an up-converted return signal occupying a frequency band at least several times higher than the frequency band of said return signal; said first and second filter circuit means each includes a frequency converter and oscillator for converting the signal band of said converted return signal to a frequency band such that the center frequency of the partial power band to be measured is converted to a preselected lower frequency, and a bandpass filter having a center frequency at said preselected lower frequency and a preselected bandwidth corresponding to the width of said partial power band to be measured, said oscillator being gated by said gate signal to operate only during the period thereof.

9. The system of claim 8, wherein said clock circuit means includes a clock signal generator and a clock signal divider for generating a first clock signal at a frequency corresponding to said preselected frequency of said modified carrier signal and second and third clock signals for supplying clock pulses respectively to said rise time circuit means and said duration time circuit means with said second clock signal having a frequency twice that of said third clock signal; and said oscillator signal means includes a clock gate receiving first clock signal and said gate signal for producing a gated clock output signal during said gate signal duration and a waveform filter coupled to the output of said clock gate to produce a substantially sine wave input to said frequency converter.

10. The system of claim 8, wherein each of said integrator circuit means includes an integrator circuit and a gating circuit responsive to said gate signal for coupling the respective input envelope signal to said integrator circuit only during the interval of said gate signal.

11. In a method of analyzing ultrasonic return signals characterizing a structure being examined, the steps of:
measuring in an analog manner the partial amount of signal power in at least a first preselected band of the frequency spectrum of the return signal;
measuring in a digital manner at least one preselected feature of the waveform of said return signal;
converting said digital waveform feature measurement to a corresponding analog waveform feature value;
combining said analog partial signal power measurement with said analog waveform feature value in accordance with a preselected algorithm to produce a test statistic; and
registering a decision on a preselected characteristic of said structure on the basis of the value of said test statistic; said algorithmic combination being preselected on the basis of experimental data demonstrating a substantial degree of discrimination in said test statistic signal value for said preselected characteristic of said structure.

12. The method of claim 11, wherein said step of measuring the partial amount of signal power includes the steps of measuring the amount of signal power in at least one preselected band of the frequency spectrum of the return signal, measuring the total signal power in the return signal; and dividing the measured band power signal by the total power signal.

13. The method of claim 11, wherein prior to performing the step of measuring in a digital manner at least one preselected feature of the waveform of said return signal is performed the step of normalizing the return signal to a fixed peak signal level; and wherein said step of measuring at least one preselected feature of the waveform of said return signal includes the steps of:
detecting in an analog manner the envelope of said normalized return signal;
measuring digitally the rise time of said normalized return signal envelope; and
measuring digitally the duration time of said normalized return signal envelope.

14. In a method of analyzing ultrasonic return signals characterizing a structure being examined, the steps of:
normalizing the ultrasonic return signal to a fixed peak signal level;
converting the normalized return signal to a frequency band at a position at least several times higher than the position of the original return signal;
separately converting the up-converted return signal down to two separate frequency bands such that the center frequency of each of two preselected partial band of the original return signal is at a preselected lower frequency point;
separately filtering the frequency downconverted return signals to isolate signal information in said preselected partial frequency band;
separately detecting the envelopes of the normalized return signal and said partial frequency band signals;
separately squaring the envelopes of the total signal and the partial frequency band signals;
separately integrating the squared partial band signal envelopes and the total signal envelope;
dividing each of the integrated partial band signal envelopes by the integrated total signal envelope to produce partial band power values;
digitally measuring the rise time and the duration time of the total signal envelope;
converting the digital duration time and rise time measurements to analog values;
combining the partial signal power values with the analog values of rise time and duration time in accordance with a preselected algorithm to produce a test statistic; and
registering a decision on a preselected characteristic of said structure being examined on the basis of the test statistic; said algorithmic combination being preselected on the basis of experimental data demonstrating a substantial degree of discrimination in said test statistic signal value for said preselected characteristic of said structure.

15. Apparatus for measuring the partial amount of signal power in a preselected band of the frequency spectrum of an ultrasonic return signal comprising:
normalizing circuit means including a frequency converter and local oscillator signal means coupled thereto for producing a normalized upconverted signal having a fixed peak signal level and occuping a frequency band at least several times higher than the frequency band of the original return signal;

a second frequency converter and local oscillator circuit means for downconverting said normalized, upconverted return signal to a lower frequency band such that the center frequency of the partial power band to be measured is converted to a preselected lower frequency;

a bandpass filter coupled to the output of said frequency down-converter and having a center frequency at said preselected lower frequency and a preselected bandwidth corresponding to the width of said partial power band to be measured;

first envelope circuit means coupled to the output of said bandpass filter for detecting the envelope of the output signal therefrom and producing a partial band envelope signal;

second envelope circuit means coupled to the output of said normalizing circuit means for detecting the envelope of said normalized, upconverted return signal for producing a total envelope signal;

first squaring circuit means for squaring said partial band envelope signal to produce a squared partial band envelope signal;

second squaring circuit means for squaring said total envelope signal to produce a squared total envelope signal;

first integrator circuit means coupled to said first envelope circuit means for integrating said squared partial band envelope signal to produce a measured band power signal;

second integrator circuit means coupled to said second envelope circuit means for integrating said squared total envelope signal to produce a total power signal;

an analog divider coupled to the outputs of said first and second integrator circuit means for dividing said measured band power signal by said total power signal to produce a partial power band signal.

16. In a system for analyzing output signals from an ultrasonic test instrument representing ultrasonic return signals characterizing a structure being examined and which output signals may contain return signal pulse waveforms having two separate peaks associated with either a single pulse or two separate pulses;

gate signal generator means for generating a GATE signal having selectable starting time position and duration to bracket the segment of the output signal containing a return signal pulse waveform to be analyzed;

normalizing circuit means gated by said GATE signal for normalizing said return signal pulse waveform to a fixed peak signal level based on the highest peak levels;

envelope circuit means for detecting the envelope of said normalized return signal pulse waveform;

first comparator circuit means for comparing said normalized pulse envelope with a preselected threshold signal level for producing a HIGH output signal when said normalized signal exceeds said threshold level and a LOW output signal when said normalized envelope signal is below said threshold level;

second comparator circuit means for comparing said normalized envelope signal with a preselected peak signal level for producing a HIGH output signal when said normalized envelope is below said peak level and a LOW output signal when said normalized envelope exceeds said peak level;

a valid pulse latch receiving the output signals from said first and second comparator circuit and being placed in a set condition when said output signal from said second comparator circuit makes a HIGH to LOW signal transition and being placed in a reset condition when said output signal from said first comparator circuit makes a HIGH to LOW signal transition;

clock circuit means for generating rise time clock signal and duration time clock signals;

duration counter means adapted to count said duration clock pulses;

rise time counter means adapted to count said rise time clock pulses;

first logic means for signaling said duration counter to count said duration clock pulses during the HIGH signal period from said first comparator circuit;

second logic circuit means for signalling said rise time counter circuit to count said rise time clock pulses during each period that said HIGH level of said output signal from said first comparator circuit coincides with a reset state of said valid pulse latch;

an end of pulse signal generator responsive to the changing of said valid pulse latch from a set to a reset condition to generate an end of pulse signal condition;

a pulse counter coupled to said gate signal generator and said end of pulse signal generator and being normally in a pulse one count state until set into a pulse two count state by the termination of said end of pulse signal;

a duration count register adapted to store the duration count accumulated in said duration count circuit;

a rise time count register adapted to store the rise time count accumulated in said rise time counter;

logic circuit means for causing said duration register circuit and said rise time register circuit to store said accumulated duration count and rise time count in response to the coincidence of said end of pulse signal and said pulse one count state of said pulse counter;

reset circuit means for resetting said duration counter circuit and said rise time counter circuit at the termination of said end of pulse signal;

a peak signal sample and hold circuit receiving said normalized pulse envelope and operative during said pulse one count state to store the peak value of the return signal waveform during that period;

third comparator circuit means for comparing the stored peak signal level in said peak sample and hold circuit with the normalized pulse envelope signal and producing a HIGH output whenever the normalized signal envelope exceeds said stored first peak signal and a LOW output whenever said envelope is less than stored peak signal;

fourth logic circuit means including a latch receiving the output of said pulse counter and said third comparator circuit for generating a latched pulse two higher signal whenever the peak of said normalized pulse envelope exceeds the level of the stored first peak signal during the second pulse period of said pulse counter;

fifth logic circuit means for generating a register clock signal upon coincidence of said latched pulse two higher signal and a second end of pulse signal during said second pulse period for causing a new duration count and rise time count to be entered into said duration count and rise time count registers.

* * * * *